United States Patent
Bennedbæk-Jensen et al.

(10) Patent No.: US 9,402,402 B2
(45) Date of Patent: Aug. 2, 2016

(54) PROCESS FOR PRODUCING A BAKED PRODUCT HAVING INCREASED FLAVOR STABILITY WITH CATALASE AND PHOSPHOLIPASE

(75) Inventors: Sidsel Langballe Bennedbæk-Jensen, Hedehusene (DK); Henrik Østdal, Virum (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 13/810,272

(22) PCT Filed: Jul. 19, 2011

(86) PCT No.: PCT/EP2011/062342
§ 371 (c)(1),
(2), (4) Date: Mar. 25, 2013

(87) PCT Pub. No.: WO2012/010593
PCT Pub. Date: Jan. 26, 2012

(65) Prior Publication Data
US 2013/0216651 A1  Aug. 22, 2013

Related U.S. Application Data

(60) Provisional application No. 61/366,323, filed on Jul. 21, 2010.

(30) Foreign Application Priority Data

Jul. 21, 2010 (EP) ..................................... 10170282

(51) Int. Cl.
A21D 8/04 (2006.01)
C12N 9/08 (2006.01)
C12N 9/16 (2006.01)

(52) U.S. Cl.
CPC .............. *A21D 8/042* (2013.01); *C12N 9/0065* (2013.01); *C12N 9/16* (2013.01); *C12Y 111/01006* (2013.01); *C12Y 301/04* (2013.01)

(58) Field of Classification Search
CPC ..... A23V 2002/00; A21D 8/042; A21D 2/00; A21D 10/002; A23L 1/105; A23L 1/1055; C12Y 111/01006; C12Y 301/01004; C12Y 301/04003; C12Y 302/01001; C11D 3/386; C12N 9/2414; A23C 9/1213

USPC ........................... 426/20, 61, 28, 18; 435/192
See application file for complete search history.

(56) References Cited

U.S. PATENT DOCUMENTS

| | | | | |
|---|---|---|---|---|
| 3,512,992 A | * | 5/1970 | Cooke et al. | ..................... 426/20 |
| 5,571,719 A | * | 11/1996 | Christensen et al. | .......... 435/264 |
| 5,624,684 A | | 4/1997 | Fulsz | |
| 2001/0055635 A1 | * | 12/2001 | Spendler et al. | ................ 426/20 |
| 2002/0197289 A1 | | 12/2002 | Chevalier et al. | |
| 2009/0038023 A1 | | 2/2009 | Weiner et al. | |

FOREIGN PATENT DOCUMENTS

| | | |
|---|---|---|
| EP | 0 468 731 A1 | 1/1992 |
| EP | 0 686 348 A1 | 12/1995 |
| EP | 1 530 905 A1 | 5/2005 |
| EP | 2 138 245 A1 | 12/2009 |
| JP | 6201 2720 | 1/1987 |
| JP | 6201 2721 | 1/1987 |
| JP | 10-084846 | 4/1998 |
| JP | 1104 6686 | 2/1999 |
| JP | 2000 300158 | 10/2000 |
| JP | 2001 211814 | 8/2001 |
| JP | 2002 102324 | 4/2002 |
| WO | 2005/080540 A1 | 9/2005 |
| WO | 2007/101846 A1 | 9/2007 |
| WO | 2008/137846 A2 | 11/2008 |

OTHER PUBLICATIONS

JP 10-084846—WPI Acces No. 1998-264746 (1998).
JP 11 046686 A—WPI Access No. 1999-208034 (1999).
JP 2000-300158—Access No. 2001-084434 (2000).
JP 2001-211814—WPI Acces No. 2001-62033 (2001).
JP 2002-102324—WPI Access No. 2005-541205 (2002).
JP 62012720 A—WPI Access No. 1987-059541 (1987).
JP 62012721 A—WPI Access No. 1987-059542 (1987).

* cited by examiner

*Primary Examiner* — Hamid R Badr
(74) *Attorney, Agent, or Firm* — Kristin McNamara

(57) ABSTRACT

The present invention relates to a process for producing a baked product having increased flavor stability comprising the steps of: (a) preparing a dough comprising flour, water, an enzyme preparation having catalase activity and an enzyme preparation having phospholipase activity; and (b) baking the dough to obtain the baked product.

9 Claims, No Drawings

PROCESS FOR PRODUCING A BAKED PRODUCT HAVING INCREASED FLAVOR STABILITY WITH CATALASE AND PHOSPHOLIPASE

CROSS-REFERENCE TO RELATED APPLICATIONS

This application is a 35 U.S.C. 371 national application of PCT/EP2011/062342 filed Jul. 19, 2011 which claims priority or the benefit under 35 U.S.C. 119 of European application no. 10170282.7 filed Jul. 21, 2010 and U.S. provisional application No. 61/366,323 filed Jul. 21, 2010, the contents of which are fully incorporated herein by reference.

FIELD OF THE INVENTION

The present invention relates to a process for preparing a baked product made from dough. More particularly, it relates to a process for preparing a baked product having increased flavor stability.

BACKGROUND OF THE INVENTION

In the preparation of bread and other baked products from dough, it is generally desirable to increase the shelf life of the baked product. For that purpose maltogenic alpha-amylase is often added to the dough. However, bread under storage may develop a rancid flavor or even taste. This tendency to develop rancid flavor or taste under storage is further increases when lipolytic enzymes, such as phospholipases are used for e.g. dough strengthening.

It is therefore an object of the present invention to provide a bread making process which can be free from the above disadvantage.

SUMMARY OF THE INVENTION

Accordingly, in a first aspect the invention relates to a process for producing a baked product having increased flavor stability comprising the steps of; (a) preparing a dough comprising flour, water and an enzyme preparation which has catalase activity and phospholipase activity, and; (b) baking the dough to obtain the baked product.

In a second aspect the invention relates to an enzyme preparation comprising a catalase activity and a phospholipase activity.

In a third aspect the invention relates to a baking composition comprising flour and the enzyme preparation of the preceding aspect.

In a fourth aspect the invention relates to use of the baking composition of the preceding aspect for preparing a dough.

DETAILED DESCRIPTION OF THE INVENTION

Dough

Dough generally comprises flour or meal such as wheat flour, wheat meal, corn flour, corn starch, rye meal, rye flour, oat flour, oat meal, soy flour, sorghum meal, sorghum flour, potato meal, potato flour or potato starch.

The dough may be fresh, frozen or par-baked.

The dough is normally a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may also comprise other conventional dough ingredients, e.g.; proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is equally applicable to a dough which is made without addition of fat.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin.

In a preferred embodiment, the dough comprises wheat flour; preferably 10% (w/w) or more of the total flour content is wheat flour, preferably at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or preferably at least 95% (w/w) of the flour is wheat flour.

The dough may be prepared applying any conventional mixing process, such as the continuous mix process, straight-dough process, or the sponge and dough method.

Flavor Stability

Increased flavor stability is defined as a reduced tendency to develop rancid flavor and/or taste during storage. The tendency to develop rancid flavor and/or taste during storage may be assessed e.g., at day 7, day 14 and/or day 21 after baking, e.g., by sensory analysis.

Catalase

A catalase for use in the invention belongs to EC 1.11.1.6 and catalyses the reaction $2\ H_2O_2 = O_2 + 2\ H_2O$.

The catalase preparation is preferably substantially free of glucose oxidase activity. A catalase preparation substantially free of glucose oxidase activity comprises less than 10%, less than 1%, less than 0.1%, or even less than 0.01% glucose oxidase based on catalase and glucose oxidase enzyme protein (w/w). A preparation substantially free of glucose oxidase comprises none or only insignificant amounts of glucose oxidase activity. A preparation substantially free of glucose oxidase when used in the process of the present invention will result in no detectable effect of any glucose oxidase activity present in the composition. Preferably the preparation substantially free of glucose oxidase comprises no measurable glucose oxidase activity.

Preferably the catalase is a microbial catalase, such as a catalase isolated from a fungi or a bacteria. Preferably the catalase is derived from a strain of *Scytalidium* sp., preferably *S. thermophilum*, a strain of *Aspergillus* sp., preferably *A. niger*, a strain of *Micrococcus* sp., preferably *M. luteus*.

Preferably the enzyme composition comprising catalase without, or substantially free of glucose oxidase is a mono component composition resulting from purification of an enzyme composition derived from a non-recombinant production strain. Methods for purification of polypeptides including enzymes are well known to the skilled person.

More preferably the enzyme composition comprising catalase is produced by recombinant techniques. By recombinant techniques an enzyme composition comprising essentially pure catalase, such as a composition without, or substantially free of glucose oxidase may be obtained. Methods for recombinant production of polypeptides including enzymes are well known to the skilled person.

A suitable catalase is derived from *Scytalidium* sp. and disclosed in WO 1992/017571 or in WO 1996/34962. Preferably the enzyme composition comprising catalase activity comprises the polypeptide disclosed as Sequence Number 2 of WO 1996/34962 or a polypeptide having catalase activity and at least 50%, at least 60%, at least 70%, at least 75%, at least 80%, at least 85%, at least 90%, at least 95% at least 96%, at least 97%, at least 98%, or even at least 99% identity to the polypeptide disclosed as Sequence Number 2 of WO 1996/34962.

A suitable recombinant catalase composition substantially free of glucose oxidase is available as Terminox Ultra™ from Novozymes A/S.

The catalase may be added in the amount of 0.02-200 mg enzyme protein (EP)/kg dough, preferably 0.2-20 mg EP/kg dough, more preferably 1-10 mg EP/kg dough. The catalase may be added in the amount of 1 CIU to 10 mill CIU/kg dough, preferably 10 CIU to 1 mill CIU/kg dough, more preferably 100 CIU to 0.1 mill CIU/kg dough, and yet more preferably 1.000 CIU to 10.000 CIU/kg dough.

Phospholipases

The phospholipase activity may be phospholipase A1 (EC 3.1.1.32) activity, or phospholipase A2 (EC 3.1.1.4) activity. Most preferably the additional enzyme has phospholipase A1 activity, e.g. such as the *Fusarium oxysporum* phospholipase disclosed in WO 1998/26057. Preferably the enzyme composition comprising the phospholipase activity comprises the polypeptide disclosed as Sequence Number 2 of WO 1998/26057 or a polypeptide having phospholipase activity and at least 50%, at least 60%, at least 70%, at least 75%, at least 80%, at least 85%, at least 90%, at least 95% at least 96%, at least 97%, at least 98%, or even at least 99% identity to the polypeptide disclosed as Sequence Number 2 of WO 1998/26057.

Suitable commercial phospholipase preparations are LIPOPAN F™ and LIPOPAN Xtra™. Both are available from Novozymes. Also suitable is the phospholipase composition PANAMORE™ available from DSM.

It is preferred that the dough comprises up to 500 ppm of the phospholipase; preferably up to 400 ppm, 300 ppm, 200 ppm, 100 ppm, 80 ppm, 40 ppm, 20 ppm, or more preferably up to 10 ppm of the phospholipase.

The phospholipase may be added in the amount of 0.001-200 mg enzyme protein (EP)/kg dough, preferably 0.005-20 mg EP/kg dough, more preferably 0.01-10 mg EP/kg dough. The phospholipase may be added in the amount of 1 LEU to 10 mill LEU/kg dough, preferably 10 LEU to 1 mill LEU/kg dough, more preferably 100 LEU to 0.1 mill LEU/kg dough, and yet more preferably 1.000 LEU to 10.00 LEU/kg dough.

Maltoqenic Alpha-Amylase

The maltogenic alpha-amylase may be derived from *Bacillus stearothermiphilus* as described in EP 494233

The maltogenic amylase may be added in a sufficient amount such that the baked product produced there from has a degree of firmness, as measured using the Texture Analyzer method described herein, that is comparable or less than that compared to a control baked product prepared from dough without the added combination of anti-staling amylase and peptidase, and this degree of firmness lasts for at least 4 to 21 days after baking, and preferably 14 to 21 days after baking.

In one embodiment, the maltogenic alpha-amylase is added in an amount of 0.1-10,000 MANU, preferably 1-5000 MANU, more preferably 5-2000 MANU, and most preferably 10-1000 MANU, per kg of flour. One MANU (Maltogenic Amylase Novo Unit) may be defined as the amount of enzyme required to release one micromol of maltose per minute at a concentration of 10 mg of maltotriose substrate per ml of 0.1 M citrate buffer, pH 5.0 at 37° C. for 30 minutes.

A suitable maltogenic alpha-amylase may be derived from *Bacillus stearothermiphilus* as described in EP 494233 or a variant thereof as described in WO 1999/43794. The *B. stearothermiphilus* maltogenic amylase is commercially known as Novamyl™ (available from Novozymes A/S). Typically, Novamyl™ is added in an amount that is at least 100 ppm/kg. In one embodiment, Novamyl™ is added in an amount that is up to 5000 MANU/kg. In one embodiment, Novamyl™ is added in an amount that is in a range of at least 100 MANU/kg flour to about 3000 MANU/kg flour.

In one embodiment, the maltogenic alpha-amylase is the enzyme commercially known as Opticake™ (available from Novozymes). Typically, Opticake™ is added in an amount that is at least 333 MANU/kg. In one embodiment, Opticake™ is added in an amount that is up to 666 MANU/kg. In one embodiment, Opticake™ is added in an amount that is at least 333 MANU/kg but less than 666 MANU/kg.

Additional Enzymes

Optionally, one or more additional enzyme(s) may be used together with the catalase. An additional enzyme may be an amylase, such as an alpha-amylase, amyloglucosidase, a beta-amylase, a cyclodextrin glucanotransferase, or the additional enzyme may be a peptidase, in particular an exopeptidase, a transglutaminase, a lipolytic enzyme, a cellulase, a hemicellulase, in particular a pentosanase such as xylanase, a protease, a glycosyltransferase, a branching enzyme (1,4-alpha-glucan branching enzyme), a 4-alpha-glucanotransferase (dextrin glycosyltransferase) or an oxidoreductase, e.g., a peroxidase, a laccase, a pyranose oxidase, a lipoxygenase, or an L-amino acid oxidase.

The additional enzyme may be of any origin, including mammalian and plant, and preferably of microbial (bacterial, yeast or fungal) origin and may be obtained by techniques conventionally used in the art.

Baked Product

The process of the invention may be used for producing any kind of baked product prepared from dough, either of a soft or a crisp character, either of a white, light or dark type. The term baked product is understood to include any dough based products which are baked, steamed or fried. Examples are bread (in particular white, whole-meal or rye bread), typically in the form of loaves or rolls, French baguette-type bread, pita bread, tortillas, cakes, pancakes, biscuits, cookies, pie crusts, crisp bread, steamed bread, doughnuts, pizza and the like.

A preferred embodiment relates to the process of the invention wherein the baked product, has an improved flavor and/or taste after 1 week or more, 2 weeks or more, or 3 weeks or more, when compared to an otherwise identical control bread or baked product without catalase, as determined in Example 1.

Enzyme Preparation

The invention provides an enzyme preparation comprising a catalase and an enzyme having phospholipase activity and optionally a maltogenic alpha-amylase as described above, for use as a baking additive in the process of the invention. Preferably, the enzyme preparation is substantially free of glucose oxidase activity.

The enzyme preparation may be in the form of a granulate or agglomerated powder. It preferably has a narrow particle size distribution with more than 95% (by weight) of the particles in the range from 25 to 500 microns.

Granulates and agglomerated powders may be prepared by conventional methods, e.g., by spraying the enzymes onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy.

The enzyme preparation may also be in the form of a liquid aqueous solution.

Baking Composition

The present invention further relates to a baking composition comprising flour together with a catalase and a phospholipase. The baking composition may contain other dough-improving and/or bread-improving additives, e.g., any of the additives, including enzymes, mentioned above. The baking composition may be e.g., a dough, a flour composition, or a flour pre-mix, or a bread improver.

Assay for Glucose Oxidase Activity (GODU)

Glucose-oxidase Unit (GODU) is the amount of enzyme, which oxidizes 1 micromol of beta-D-Glucose per minute.

Glucose-oxidase (beta-D-glucose: oxygen-1-oxido-reductase, EC 1.1.3.4.) oxidises beta-D-glucose in the presence of oxygen to delta-glucono-lactone and hydrogen-peroxide. The generated hydrogen-peroxide oxidises ABTS-R (2,2-Azino-di-(3-ethylbenzthiazoline)-6-sulfonate) in the presence of peroxidase (POD). This generates a green-blue colour, which is measured photometrically at 405 nm.

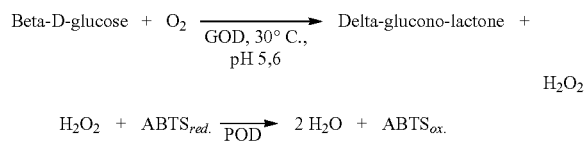

Reaction Conditions

| Substrate | D-glucose 90 mM (16.2 g/L) |
|---|---|
| ABTS | 1.25 mM (688 mg/L) |
| Glucose-oxidase | 0.0061-0.0336 GODU/mL |
| Peroxidase (POD) | 2930 U/L |
| Buffer | Acetate, 100 mM |
| pH | 5.60 ± 0.05 |
| Temperature | 30° C. ± 1 |
| Reaction time | 36 sec. (8 × 4.5 sec.) |
| Wavelength | 405 nm |

A detailed description of the GODU standard method (EB-SM-0244.02) is available upon request from Novozymes A/S.

Degree of Sequence Identity

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

Assay for Phospholipase Activity

Phospholipase activity: The term "phospholipase activity" is defined herein as enzymatic activity that catalyzes the release of fatty acyl groups from a phospholipid. A phospholipase may also catalyze the release of fatty acyl groups from other lipids.

Phospholipase activity (LEU) is measured as the release of free fatty acids from lecithin at pH 8 and 40° C. Phospholipase activity is measured in LEU (LEcitase Units) relative to an enzyme standard (Lecitase) of declared activity.

Lecithin substrate emulsion is prepared by homogenizing 20 g lecithin (L-alpha-phosphatidyl-choline from soybean, Sigma Chemicals, P5638) in 1020 mL (6.2 mM $CaCl_2$, 3.1 mM sodium deoxycholate) using a Silverson L4R homogenizer for 10 min at maximum speed. pH of the emulsion is adjusted to approximately pH 7.5 and the emulsion is kept at 40° C. on a magnetic stirrer throughout the analysis. Twenty-five mL substrate solution is transferred automatically to the titration vessel with temperature control (40° C.) of a Metrohm 2 Titrator and 0.1 M NaOH is automatically added to obtain a pH of 8. The reaction is initiated by addition of 1 mL appropriate diluted enzyme sample (diluted in 0.001 M HCl or water) and the reaction is followed by the rate of 0.1 M NaOH consumption. The NaOH consumption is transformed to LEU/mL by the use of a standard curve prepared from a Lecitase standard.

Alternatively phospholipase activity may be determined using 4% L-alpha-phosphatidylcholine (plant lecithin from Avanti Polar Lipids Inc.), 4% Triton X-100, 5 mM CaCl2 in 50 mM HEPES, pH 7 is added 50 microL enzyme solution diluted to an appropriate concentration in 50 mM HEPES, pH 7. The samples are incubated for 10 min at 30° C. and the reaction stopped at 95° C. for 5 min prior to centrifugation (5 min at 7000 rpm). Free fatty acids are determined using the NEFA C kit from Wako Chemicals; 25 microL reaction mixture is added 250 microL Reagent A and incubated 10 min at 37° C. Subsequently, 500 microL Reagent B is added and the sample is incubated again, 10 min at 37° C. The absorption at 550 nm is measured using an HP 8452A diode array spectrophotometer. Samples are run in at least in duplicates. Substrate and enzyme blinds (preheated enzyme samples (10 min at 95° C.)+substrate) are included. Oleic acid is used as a fatty acid standard. 1 PHLU equals the amount of enzyme capable of releasing 1 micromole of free fatty acid/min at these conditions.

Assay for Catalase Activity

Catalase activity may be measured in CIU. Catalase catalyzes the first order reaction:

$$2H_2O_2 \rightarrow 2H_2O + O_2$$

The degradation of hydrogen peroxide is monitored using spectrophotometry at 240 nm. The time taken for a specified decrease in absorbance at a specified $H_2O_2$ concentration is an expression of catalase activity. One CIU is defined as the enzyme activity that will degrade one micromole $H_2O_2$ per minute at pH 7.0 and 25° C., reducing the $H_2O_2$ concentration from 10.3 to 9.2 mM.

Reaction Conditions:

| Enzyme concentration | approx. 100 CIU/mL |
|---|---|
| Substrate concentration | 10.3 mM $H_2O_2$ |
| Buffer | 50 mM phosphate |
| Temperature | 25° C. |
| pH | 7.0 |

Detection:

| Wavelength | 240 nm |
|---|---|
| Absorbance range | 0.450-0.400 |
| Time range | 0.267-0.400 minutes (16-24 seconds) |

A detailed description of the CIU standard method (EB-SM-0250.02/01) is available upon request from Novozymes A/S.

EXAMPLES

Enzymes

All enzymes applied were from Novozymes A/S, Denmark. Terminox Ultra™ is a catalase preparation substantially free of glucose oxidase. The catalase is derived from *Scytalidium* sp. and disclosed in WO 1992/017571. Lipopan F™ is a phospholipase derived from *Fusarium oxysporium* and disclosed as Sequence Number 2 in WO 1998/26057. Fungamyl Super MA™ comprises fungal alpha-amylase and xylanase. Novamyl™ 10.000 BG is an anti-staling maltogenic alpha-amylase.

Bread Samples

Whole wheat bread was prepared based on the ingredients shown in Table 1. The bread was prepared according to a sponge and dough procedure. Part of the flour (60% of total flour) was mixed with 62% of the total water, yeast and sodium stearoyl-2-lactylate to form the sponge. The sponge was placed in a proofing cabinet (27° C. and 86% RH) for 3 hours. Subsequently, the rest of the ingredients were mixed in and the dough was further proofed for 45 min (42° C. and 86% RH) before baking baked for 25 min at 225 C in a reel oven (Reed Oven Co, US).

Bread was prepared in two separate experiments. The first experiment included phospholipase (375 LEU/kg dough) and catalase (2700 CIU/kg dough) added separately and compared to a control with neither phospholipase nor catalase. In the second experiment phospholipase and catalase were added separately and compared to bread prepared with a combination of the two enzymes using the same enzyme concentrations as in Experiment 1.

TABLE 1

List of ingredients for production of whole wheat bread [% of total (w/w)]

| | | | |
|---|---|---|---|
| Whole wheat flour | 53.84 | Sodium stearoyl-2-lactylate | 0.27 |
| Water | 33.89 | Ascorbic acid | 0.003 |
| Salt | 1.08 | Calcium propionate | 0.13 |
| Glucose syrup | 4.31 | Mono and di-glycerides | 0.54 |
| Cane syrup | 2.15 | Azo-dicarbon-amide | 0.002 |
| Soy oil | 1.08 | Novamyl 10.000 BG | 0.01 |
| Yeast | 2.69 | Fungamyl Super MA | 0.002 |

Propanoic acid was added to the dough to prevent microbial spoilage and after baking the bread loaves were treated on the surface with 6% calcium-sorbate solution. Subsequent to surface treatment the bread was further baked for 1 min to evaporate excess water from the sorbate-treatment. The bread was packed for storage in modified atmosphere (nitrogen) after cooling using food grade vacuum plastic bags. Samples were collected over a 3 week period providing samples of fresh bread (2 hour after baking) and samples stored for 1 day, 1 week, 2 weeks and 3 weeks.

Sensory Analysis

Descriptive sensory profiling was used to detect changes in the flavor of the bread during storage. The bread loaves were sliced to a thickness of approximately 1.2 cm on a slicing machine. The end pieces of each bread loaf (approximately 5 cm) were discarded.

An experienced sensory panel was used for evaluation of bread samples. The panel consisted of 9 experienced assessors. The sensory profiling was performed in a sensory evaluation laboratory, which fulfils requirements according to international standards (ASTM, 1986; ISO, 1988).

The list of attributes was divided into four categories: 'Aroma' (nasal perception), 'Flavor' (oral and retro nasal perception), 'Taste' (oral perception), and 'Sensation' (physical sensation in the nose or oral cavity).

For each type of bread the assessors evaluated bread stored for: '0 weeks', '1 week', '2 weeks', and '3 weeks' times eight replicates over a two days period (a total of 32 samples per assessor). The assessors evaluated the samples at individual speed by descriptive analysis on an unstructured 15.0 cm line scale labelled on the left by 'low' and on the right with the term 'high'. Ratings were registered on a direct computerised registration system (Fizz software, 2.30C, Biosystemes, Couternon, France).

Results

Experiment 1: Bread was prepared with phospholipase and catalase, and a control. The observations from the sensory analysis of the different treatments and sampling times could be significantly separated. By the end of the 3 weeks storage period the assessors found phospholipase containing samples to be more rancid compared to control samples. The catalase treated samples were the least rancid. This show that addition of phospholipase can have a tendency to compromise the flavor profile of bread after pro-longed storage period and that addition of catalase can reduce the formation of rancid flavor attributes and thereby increasing flavor stability.

Experiment 2: Bread was prepared with phospholipase, catalase or a combination of phospholipase and catalase. Bread without enzyme addition was prepared as contros. Following 3 weeks storage the bread comprising phospholipase was conceived by the assessors as more rancid compared to bread prepared with catalase or phospholipase/catalase. This shows that the addition of catalase can mitigate the tendency to rancid flavor formation that may be observed in bread prepared with phospholipase following storage.

The invention claimed is:

1. A process for producing a baked product having increased flavor stability comprising the steps of:
   (a) adding to a dough comprising flour, water, a catalase and a phospholipase; and
   (b) baking the dough to obtain the baked product,
   wherein the baked product has increased flavor stability after one week or more as compared to a baked product prepared without the addition of enzyme preparation having catalase activity.

2. The process of claim 1, wherein the enzyme preparation having catalase activity further comprises a maltogenic alpha-amylase.

3. The process of claim 1, wherein the enzyme preparation having catalase activity is substantially free of glucose oxidase activity.

4. The process of claim 1, wherein the baked product has increased flavor stability after two weeks or more.

5. The process of claim 1, wherein the baked product has increased flavor stability after three weeks or more.

6. The process of claim 1, wherein the catalase is derived from a strain of *Scytalidium*, *Aspergillus*, or *Micrococcus*.

7. The process of claim 1, wherein the catalase is derived from a strain of *Scytalidium thermophilum*, *Aspergillus niger*, or *Micrococcus luteus*.

8. The process of claim 1, wherein the phospholipase is derived from *Fusarium oxysporum*.

9. A process for preparing a dough comprising adding an enzyme preparation having catalase activity and an enzyme preparation having phospholipase activity to flour and water.

* * * * *